United States Patent
Dasbach et al.

(10) Patent No.: US 10,369,286 B2
(45) Date of Patent: Aug. 6, 2019

(54) DRIVE UNIT FOR A DRUG DELIVERY DEVICE

(71) Applicant: SANOFI-AVENTIS DEUTSCHLAND GMBH, Frankfurt am Main (DE)

(72) Inventors: Uwe Dasbach, Frankfurt am Main (DE); George Edward Sykes, Frankfurt am Main (DE); Thomas Mark Kemp, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 411 days.

(21) Appl. No.: 14/906,935

(22) PCT Filed: Jul. 17, 2014

(86) PCT No.: PCT/EP2014/065421
§ 371 (c)(1),
(2) Date: Jan. 22, 2016

(87) PCT Pub. No.: WO2015/011023
PCT Pub. Date: Jan. 29, 2015

(65) Prior Publication Data
US 2016/0175526 A1 Jun. 23, 2016

(30) Foreign Application Priority Data
Jul. 25, 2013 (EP) .................................... 13178032

(51) Int. Cl.
*A61M 5/20* (2006.01)
*A61M 5/315* (2006.01)

(52) U.S. Cl.
CPC ...... *A61M 5/2033* (2013.01); *A61M 5/31565* (2013.01); *A61M 2005/202* (2013.01)

(58) Field of Classification Search
CPC ............ A61M 5/2033; A61M 5/31565; A61M 2005/202; A61M 5/31541;
(Continued)

(56) References Cited

U.S. PATENT DOCUMENTS 1,476,946 A * 12/1923 Bessesen ................ A61M 3/00
222/340
2,158,375 A * 5/1939 Miller ................ B65D 47/2093
222/496

(Continued)

FOREIGN PATENT DOCUMENTS

| CN | 1193917 | 9/1998 |
| EP | 1728529 | 7/2008 |

(Continued)

OTHER PUBLICATIONS

Sims et al., WO97/07838, Multi-Dose Syringe Driver, date of publication Mar. 6, 1997.*

(Continued)

*Primary Examiner* — Manuel A Mendez
(74) *Attorney, Agent, or Firm* — Fish & Richardson P.C.

(57) ABSTRACT

Described is a drive unit (1) for a drug delivery device comprising a carrier (3), a plunger (4) arranged within the carrier (3) and slidable in a direction of a longitudinal axis (A), a drive spring (5) arranged for biasing the plunger (4) in a distal direction (D) relative the carrier (3), and a drive force adaption mechanism (22) for modifying a force exerted by the drive spring (5) on the plunger (4).

14 Claims, 6 Drawing Sheets

(58) Field of Classification Search
CPC .......... A61M 5/31551; A61M 5/31543; A61M 5/20; A61M 5/24; A61M 5/3157; A61M 5/31585; A61M 5/3204; A61M 5/3158
USPC .......................................... 604/223, 134–136
See application file for complete search history.

(56) References Cited

U.S. PATENT DOCUMENTS

| | | | |
|---|---|---|---|
| 5,810,778 A | | 9/1998 | Hjertman |
| 5,814,004 A | * | 9/1998 | Tamari ................ A61M 1/0031 251/10 |
| 9,682,330 B1 | * | 6/2017 | Sherry ..................... B01D 1/30 |

FOREIGN PATENT DOCUMENTS

| | | |
|---|---|---|
| EP | 2489380 | 8/2012 |
| JP | H08-511460 | 12/1996 |
| JP | H11-514255 | 12/1999 |
| WO | WO 95/00193 | 1/1995 |
| WO | WO 97/07838 | 3/1997 |
| WO | WO2005/018721 | 3/2005 |
| WO | WO 95/03844 | 12/2006 |
| WO | WO2007/017052 | 2/2007 |

OTHER PUBLICATIONS

Remington's Pharmaceutical Sciences 17. ed. Alfonso R. Gennaro (Ed.), Mark Publishing Company, Easton, PA., U.S.A., 1985 and in Encyclopedia of Pharmaceutical Technology, 4 pages.
Rote Liste, "50. Hypophysen-, Hypothalamushormone, andere regulatorische Peptide u. ihre Hemmstoffe," Chapter 50, ed. 2008, 20 pages.
PCT International Search Report for International Application No. PCT/EP2014/065421 dated Aug. 26, 2014, 4 pages.
PCT International Written Opinion for International Application No. PCT/EP2014/065421 dated Aug. 26, 2014, 5 pages.

* cited by examiner

DRIVE UNIT FOR A DRUG DELIVERY DEVICE

CROSS-REFERENCE TO RELATED APPLICATIONS

This application is a U.S. national stage application under 35 USC § 371 of International Application No. PCT/EP2014/065421, filed on Jul. 17, 2014, which claims priority to European Patent Application No. 13178032.2, filed on Jul. 25, 2013, the entire contents of which are incorporated herein by reference.

TECHNICAL FIELD

The invention relates to a drive unit for a drug delivery device.

BACKGROUND OF THE INVENTION

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages for the user from this approach. If the user stops pressing the button/plunger, then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, hand-shaking and the likelihood of delivering an incomplete dose are reduced. In some devices the energy to deliver the fluid is provided by a spring.

When an auto-injector is driven by a spring, the spring force is usually highest at the beginning of the motion. With increasing extension of the spring the spring force decays. This may lead to variation in the delivery of the dose over the injection cycle.

There remains a need for an improved drive unit for a drug delivery device.

SUMMARY OF THE INVENTION

It is an object of the present invention to provide an improved drive unit for a drug delivery device.

The object is achieved by a drug delivery device according to claim 1.

Exemplary embodiments of the invention are given in the dependent claims.

In an exemplary embodiment, a drive unit for a drug delivery device according to the present invention comprises a carrier, a plunger arranged within the carrier (3) and slidable in a direction of a longitudinal axis (A), a drive spring arranged for biasing the plunger in a distal direction relative to the carrier, and a drive force adaption mechanism for modifying a force exerted by the drive spring on the plunger.

In an exemplary embodiment, the carrier is arranged within a case and axially constrained in a proximal direction with respect to the case.

In an exemplary embodiment, the drive force adaption mechanism is adapted to alter an initial length of the drive spring.

In an exemplary embodiment, the drive force adaption mechanism is adapted to introduce a friction force opposing a force of the drive spring. The drive force adaption mechanism comprises at least one disk-shaped insert arrangeable within the case in a fixed axial position providing a backstop for the carrier. Or, the drive force adaption mechanism comprises a cam arranged in the case rotatable about a transversal axis protruding through the case adapted to alter the axial position of the carrier relative the case depending on an angular position of the cam. Or, the drive force adaption mechanism comprises a gearbox arranged in the case for altering an axial position of the carrier relative the case. The gearbox comprises a threaded shaft on the carrier extending in a proximal direction and passing through a first bevel gear with an internal thread. The first bevel gear is driven by a second bevel gear rotatable about a transversal axis protruding through the case. Or, the drive force adaption mechanism comprises at least one resilient beam arranged on the carrier and radially outwardly biased for engaging at least one of a series of axially consecutive notches inside the case, wherein a respective hole through the case is arranged in each notch allowing for disengaging the beam from the notch. Or, the drive force adaption mechanism comprises a wedge shaped proximal end of the carrier adapted to contact a block axially fixed in the case and adapted to be transversally moved. The block is in a threaded engagement to a threaded transversal axis protruding through the case.

In an exemplary embodiment, a knob is arranged on the transversal axis (8) outside the case.

In an exemplary embodiment, the drive force adaption mechanism comprises a case beam on the case adapted to axially overlap the case on the inside, wherein a screw is transversally arranged through the case adapted to contact the case beam and press it radially inwards onto the carrier depending on a tightening of the screw.

The drive force adaption mechanism allows for influencing the drive force exerted on the plunger thus achieving a more regular injection time or an adaption of the drug delivery device to a viscosity of a drug to be delivered. Furthermore, the injection time may be adjusted (e.g. low, medium, fast).

Further scope of applicability of the present invention will become apparent from the detailed description given hereinafter. However, it should be understood that the detailed description and specific examples, while indicating exemplary embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
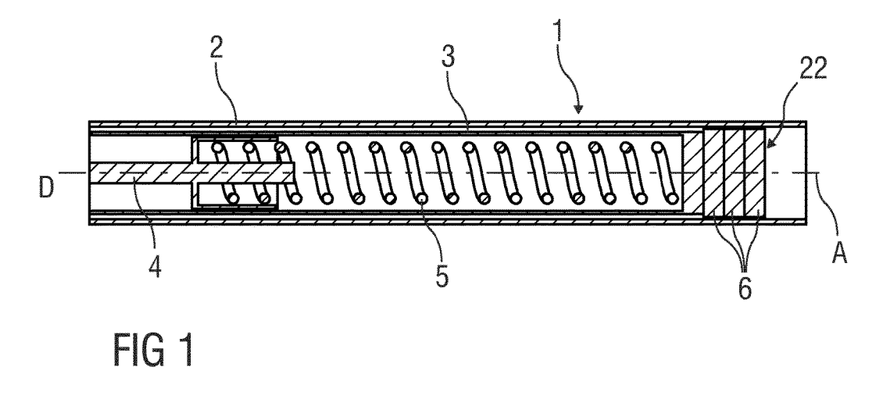
FIG. 1 is a schematic longitudinal section of a first exemplary embodiment of a drive unit for a drug delivery device.

FIG. 1 is a schematic longitudinal section of a first exemplary embodiment of a drive unit 1 for a drug delivery device. The drive unit 1 is arranged in a case 2 of the drug delivery device and comprises a tubular carrier 3, a plunger 4, arranged within the carrier 3 and slidable in a direction of a longitudinal axis A for advancing a stopper within a syringe (not illustrated). A drive spring 5 is arranged for biasing the plunger 4 in a distal direction D relative the carrier 3. A drive force adaption mechanism 22 arranged for modifying a force of the drive spring 5 comprises a number of disk-shaped inserts 6 arranged within the case 2 in a fixed axial position providing a backstop for the carrier 3 thus allowing altering the axial position of the carrier 3 relative the case 2 depending on the number of inserts 6 used. As an axial position of the plunger 4 relative the case 2 is fixed prior to release of the plunger 4, modification of the axial position of the carrier 3 within the case 2 configures the length and extent of compression of the drive spring 5. This allows for influencing the initial spring force on release of the plunger 4. The spring force is calculated by equation (1):

$$F=k(L_0-L) \tag{1}$$

with: F spring force
k stiffness constant of the spring
$L_0$ free length of the spring when unconstrained
L length of the spring Adapting the initial spring force allows for a more regular injection time or for adapting the drug delivery device to a viscosity of a drug to be delivered. Furthermore, the injection time may be adjusted (e.g. low, medium, fast).

Figure 2A:
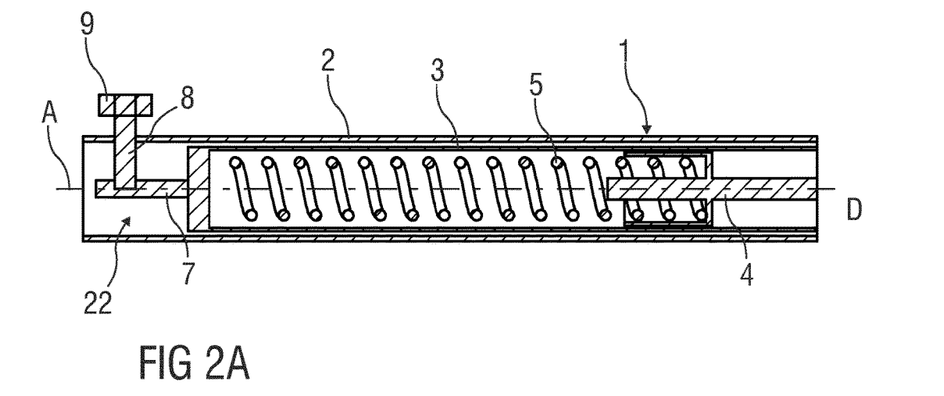
FIG. 2A is a schematic longitudinal section of a second exemplary embodiment of a drive unit for a drug delivery device.
Figure 2B:
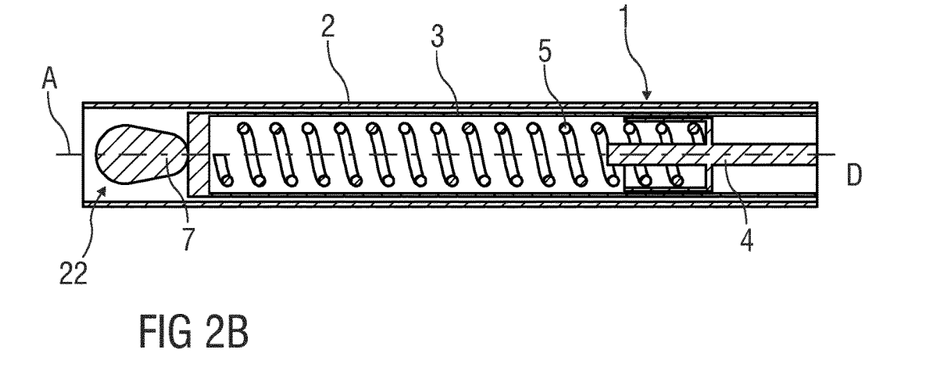
FIG. 2B is another schematic longitudinal section of the second exemplary embodiment of the drive unit for a drug delivery device.
Figure 2C:
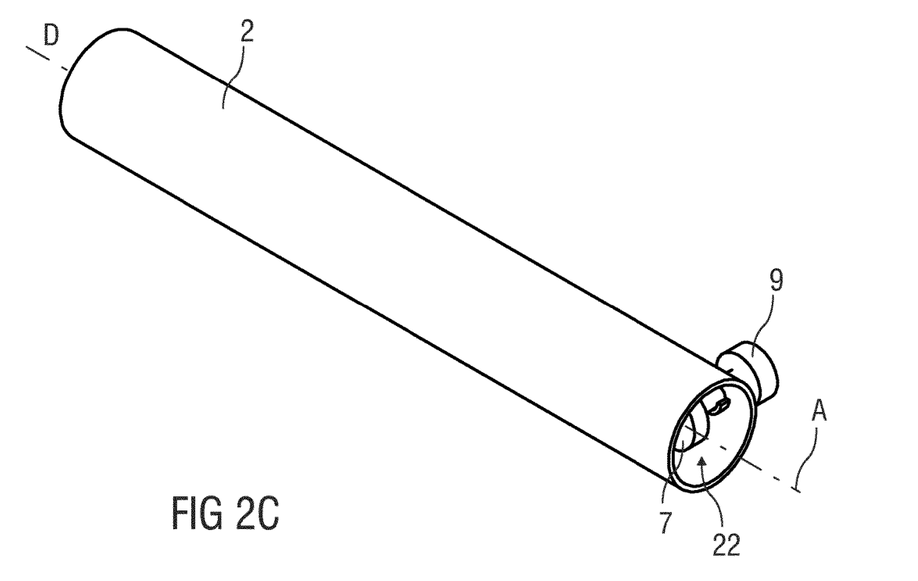
FIG. 2C is a schematic perspective view of the second exemplary embodiment of the drive unit for a drug delivery device.

FIGS. 2A and 2B are schematic longitudinal sections of a second exemplary embodiment of a drive unit 1 for a drug delivery device shown in different section planes. FIG. 2C is a related perspective view. The drive unit 1 is arranged in a case 2 of the drug delivery device and comprises a tubular carrier 3, a plunger 4, arranged within the carrier 3 and slidable in a direction of a longitudinal axis A. A drive spring 5 is arranged for biasing the plunger 4 in a distal direction D relative the carrier 3. A drive force adaption mechanism 22 arranged for modifying a force of the drive spring 5 comprises a cam 7 arranged in the case 2 rotatable about a transversal axis 8 protruding through the case 2. A knob 9 is arranged on the transversal axis 8 outside the case 2 for rotating the cam 7. Rotating the cam 7 allows for altering the axial position of the carrier 3 relative the case 2 depending on the angular position of the cam 7. As an axial position of the plunger 4 relative the case 2 is fixed prior to release of the plunger 4, modification of the axial position of the carrier 3 within the case 2 configures the length and extent of compression of the drive spring 5. This allows for influencing the initial spring force on release of the plunger 4. The spring force is calculated by equation (1) as in the first embodiment. The drive unit 1 according to the second embodiment allows for configuring the spring length and force without having to open the drug delivery device.

Figure 3:
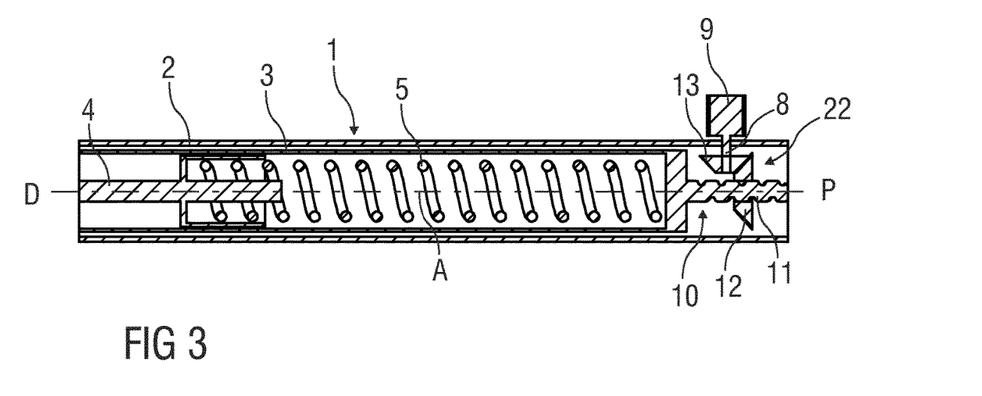
FIG. 3 is a schematic longitudinal section of a third exemplary embodiment of a drive unit for a drug delivery device.

FIG. 3 is a schematic longitudinal section of a third exemplary embodiment of a drive unit 1 for a drug delivery device. The drive unit 1 is arranged in a case 2 of the drug delivery device and comprises a tubular carrier 3, a plunger 4, arranged within the carrier 3 and slidable in a direction of a longitudinal axis A. A drive spring 5 is arranged for biasing the plunger 4 in a distal direction D relative the carrier 3. A drive force adaption mechanism 22 arranged for modifying a force of the drive spring 5 comprises a gearbox 10 arranged in the case 2 for altering an axial position of the carrier 3 relative the case 2. The gearbox 10 comprises a threaded shaft 11 on the carrier 3 extending in a proximal direction P and passing through a first bevel gear 12 with an internal thread. The first bevel gear 12 is driven by a second bevel gear 13 rotatable about a transversal axis 8 protruding through the case 2. A knob 9 is arranged on the transversal axis 8 outside the case 2 for rotating the second bevel gear 13 and thus modifying the axial position of the carrier 3 relative the case 2. As an axial position of the plunger 4 relative the case 2 is fixed prior to release of the plunger 4, modification of the axial position of the carrier 3 within the case 2 configures the length and extent of compression of the drive spring 5. This allows for influencing the initial spring force on release of the plunger 4. The spring force is calculated by equation (1) as in the first and second embodiments. The drive unit 1 according to the second embodiment allows for configuring the spring length and force without having to open the drug delivery device.

Figure 4:
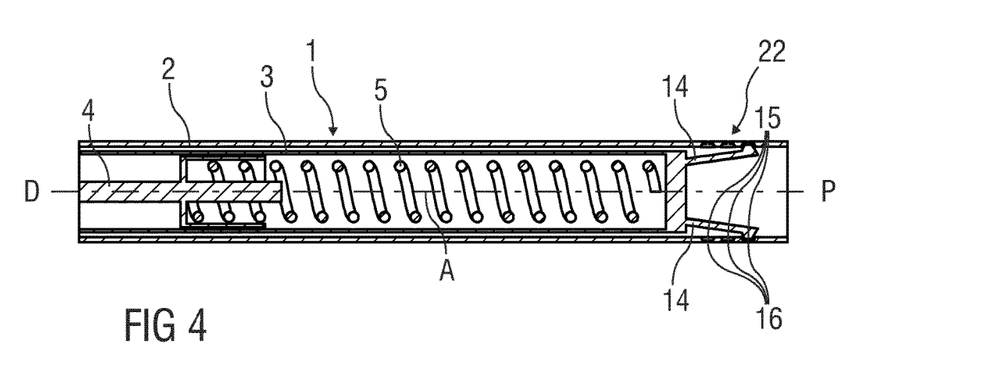
FIG. 4 is a schematic longitudinal section of a fourth exemplary embodiment of a drive unit for a drug delivery device.

FIG. 4 is a schematic longitudinal section of a fourth exemplary embodiment of a drive unit 1 for a drug delivery device. The drive unit 1 is arranged in a case 2 of the drug delivery device and comprises a tubular carrier 3, a plunger 4, arranged within the carrier 3 and slidable in a direction of a longitudinal axis A. A drive spring 5 is arranged for biasing the plunger 4 in a distal direction D relative the carrier 3. A drive force adaption mechanism 22 arranged for modifying a force of the drive spring 5 comprises one, two or more resilient beams 14 proximally arranged on the carrier 3 and radially outwardly biased for engaging into at least one of a series of axially consecutive notches 15 inside the case 2. The drive spring 5 is attempting to drive the carrier 3 in the proximal direction P but is restrained by the beams 14 engaged in the notches 15. A respective hole 16 through the case 2 is arranged in each notch 15 allowing poking the beam 14 for radially inwardly deflecting and disengaging the beam 14 from the notch 15. As the carrier 3 is biased in the proximal direction P the disengaged beam 14 will move to the next notch 15 in the proximal direction P and engage it. As an axial position of the plunger 4 relative the case 2 is fixed prior to release of the plunger 4, modification of the axial position of the carrier 3 within the case 2 configures the length and extent of compression of the drive spring 5. This allows for influencing the initial spring force on release of the plunger 4. The spring force is calculated by equation (1) as in the first, second and third embodiments. The drive unit 1 according to the second embodiment allows for configuring the spring length and force without having to open the drug delivery device.

Figure 5A:
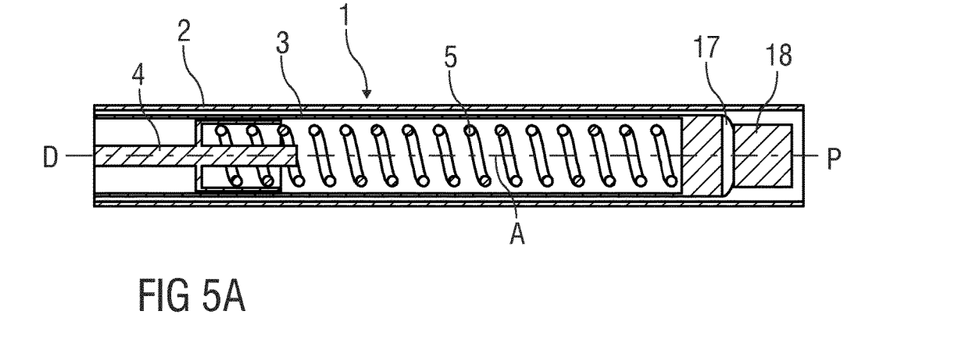
FIG. 5A is a schematic longitudinal section of a fifth exemplary embodiment of a drive unit for a drug delivery device.
Figure 5B:
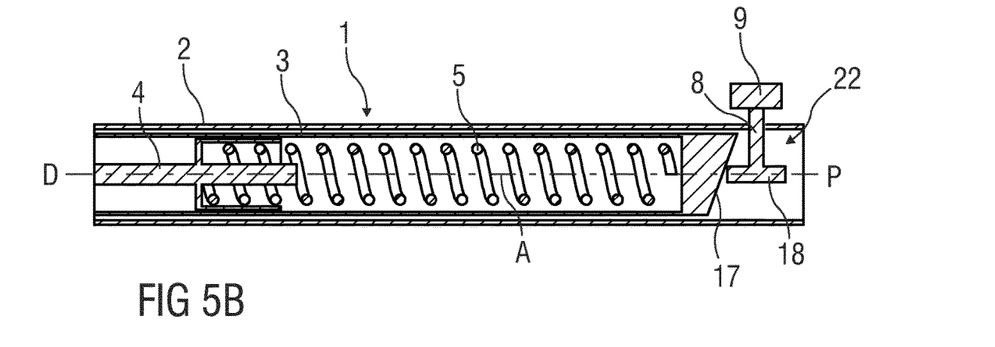
FIG. 5B is another schematic longitudinal section of the fifth exemplary embodiment of the drive unit for a drug delivery device.

FIGS. 5A and 5B are schematic longitudinal sections of a fifth exemplary embodiment of a drive unit 1 for a drug delivery device in different section planes. The drive unit 1 is arranged in a case 2 of the drug delivery device and comprises a tubular carrier 3, a plunger 4, arranged within the carrier 3 and slidable in a direction of a longitudinal axis A. A drive spring 5 is arranged for biasing the plunger 4 in a distal direction D relative the carrier 3. A drive force adaption mechanism 22 arranged for modifying a force of the drive spring 5 comprises a wedge shaped proximal end 17 of the carrier 3 adapted to contact a block 18. The block 18 is arranged on a threaded transversal axis 8 protruding through the case 2. A knob 9 is arranged on the transversal axis 8 outside the case 2 for rotating the transversal axis 8 thus moving the block 18 along the transversal axis 8. Depending on the position of the block 18 on the transversal axis 8 the axial position of the wedge shaped proximal end 17 of the carrier 3 is changed thus altering the length of the drive spring 5. As an axial position of the plunger 4 relative the case 2 is fixed prior to release of the plunger 4, modification of the axial position of the carrier 3 within the case 2 configures the length and extent of compression of the drive spring 5. This allows for influencing the initial spring force on release of the plunger 4. The spring force is calculated by equation (1) as in the first and second embodiments. The drive unit 1 according to the second embodiment allows for configuring the spring length and force without having to open the drug delivery device.

Figure 6:
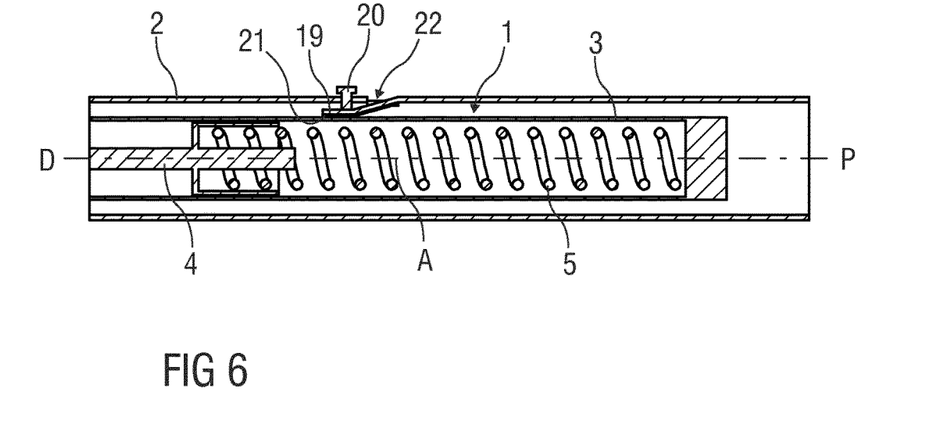
FIG. 6 is a schematic longitudinal section of a sixth exemplary embodiment of a drive unit for a drug delivery device.

FIG. 6 is a schematic longitudinal section of a sixth exemplary embodiment of a drive unit 1 for a drug delivery device. The drive unit 1 is arranged in a case 2 of the drug delivery device and comprises a tubular carrier 3, a plunger 4, arranged within the carrier 3 and slidable in a direction of a longitudinal axis A. A drive spring 5 is arranged for biasing the plunger 4 in a distal direction D relative the carrier 3. A drive force adaption mechanism 22 arranged for modifying a force exerted on the plunger 4 comprises a case beam 19 on the case 2 adapted to axially overlap the case 2 on the inside. A screw 20 through the case 2 is adapted to contact the case beam 19 and press it radially inwards onto the carrier 3 as the screw 20 is tightened. A flat inward face 21 on the case beam 19 is adapted to contact an outer surface of the carrier 3. As the screw 20 is tightened the contact force between the case beam 19 and the carrier 3 increases thereby also increasing a friction force opposing axial movement of the carrier 3 within the case 2. This friction force opposes the spring force of the drive spring 5 allowing altering the injection speed by adjusting the screw. A radial counter bearing (not illustrated) may be arranged for preventing radial movement of the carrier 3 within the case 2.

Adapting the spring force by introducing an opposing friction force allows for a more regular injection time or for adapting the drug delivery device to a viscosity of a drug to be delivered. Furthermore, the injection time may be adjusted (e.g. low, medium, fast).

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(w-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5 des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains p and c have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A drive unit for a drug delivery device, comprising:
a carrier arranged within a case and axially constrained in a proximal direction with respect to the case;
a plunger arranged within the carrier and slidable in a direction of a longitudinal axis;
a drive spring in the shape of a compression spring arranged for biasing the plunger in a distal direction relative to the carrier; and
a drive force adaption mechanism for modifying a force exerted by the drive spring on the plunger,
wherein the drive force adaption mechanism is adapted to alter an initial length of the drive spring.

2. The drive unit according to claim 1, wherein the drive force adaption mechanism comprises at least one disk-shaped insert arrangeable within the case in a fixed axial position providing a backstop for the carrier.

3. The drive unit according to claim 1, wherein the drive force adaption mechanism comprises a cam arranged in the case rotatable about a transversal axis extending through the case adapted to alter the axial position of the carrier relative to the case depending on an angular position of the cam.

4. The drive unit according to claim 3, wherein a knob is arranged along the transversal axis outside the case.

5. The drive unit according to claim 1, wherein the drive force adaption mechanism comprises a gearbox arranged in the case for altering an axial position of the carrier relative to the case.

6. The drive unit according to claim 5, wherein the gearbox comprises a threaded shaft on the carrier extending in a proximal direction and passing through a first bevel gear with an internal thread.

7. The drive unit according to claim 6, wherein the first bevel gear is driven by a second bevel gear rotatable about a transversal axis extending through the case.

8. The drive unit according to claim 1, wherein the drive force adaption mechanism comprises at least one resilient beam arranged on the carrier and radially outwardly biased for engaging at least one of a series of axially consecutive notches inside the case, wherein a respective hole through the case is arranged in each notch allowing for disengaging the beam from the notch.

9. The drive unit according to claim 1, wherein the drive force adaption mechanism comprises a wedge shaped proximal end of the carrier adapted to contact a block axially fixed in the case and adapted to be transversally moved.

10. The drive unit according to claim 9, wherein the block is in a threaded engagement to a threaded transversal axis extending through the case.

11. The drive unit according to claim 1, wherein the drive force adaption mechanism comprises a case beam on the case adapted to axially overlap the case along an inner surface of the case, wherein a screw is transversally arranged through the case adapted to contact the case beam and press the case beam radially inwards onto the carrier depending on a tightening of the screw.

12. The drive unit according to claim 1, wherein the drive force adaption mechanism is adapted to introduce a friction force opposing a force of the drive spring.

13. A drive unit for a drug delivery device, comprising:
a carrier arranged within a case and axially constrained in a proximal direction with respect to the case;

a plunger arranged within the carrier and slidable in a direction of a longitudinal axis;

a drive spring in the shape of a compression spring arranged for biasing the plunger in a distal direction relative to the carrier; and a drive force adaption mechanism for modifying a force exerted by the drive spring on the plunger, wherein the drive force adaption mechanism is adapted to introduce a friction force opposing a force of the drive spring.

14. A method comprising:

rotating a member protruding radially outward from a housing of a drug delivery device about a transverse axis extending through the housing;

the rotation of the member altering a stored spring force of a compression spring disposed within the housing; and then releasing the compression spring to advance a plunger relative to the housing in a distal direction by causing the plunger to slide in a direction of a longitudinal axis.

* * * * *